United States Patent [19]

Montgomery et al.

[11] 4,147,691
[45] Apr. 3, 1979

[54] PROCESS FOR THE EXTRACTION AND PURIFICATION OF CESALIN

[75] Inventors: Rex Montgomery; Chao-Kuo Chiang, both of Iowa City, Iowa

[73] Assignee: University of Iowa Research Foundation, Iowa City, Iowa

[21] Appl. No.: 783,511

[22] Filed: Mar. 31, 1977

[51] Int. Cl.$^2$ .................. C07G 7/00; A61K 35/78
[52] U.S. Cl. .................. 260/112 R; 424/177; 424/195; 260/123.5
[58] Field of Search .................. 424/195; 260/112 R, 260/123.5

[56] References Cited

PUBLICATIONS

Ulubelen et al., J. Pharm. Sciences, vol. 56, No. 7, pp. 914–916 (Jul. 1967).
Nature, vol. 195, pp. 281–283 (1962).

Primary Examiner—Donald B. Moyer
Attorney, Agent, or Firm—Beveridge, DeGrandi, Kline & Lunsford

[57] ABSTRACT

Pure cesalin having a high degree of anti-tumor activity is obtained by organic solvent extraction of either the whole seeds or the endosperm of the plant *Caesalpinia gilliesii*, to remove a lipid portion, extraction of the defatted endosperm with water, dialysis of the extract against water, separation of the non-dialyzable portion into a supernatant, precipitating crude cesalin from the supernatant by acidification or with ammonium sulfate, and purifying the crude cesalin by gel filtration and elution.

1 Claim, 3 Drawing Figures

PROCESS FOR THE EXTRACTION AND PURIFICATION OF CESALIN

BACKGROUND OF THE INVENTION

The present invention relates to a novel process for the extraction and purification of cesalin, a proteinaceous substance exhibiting antitumor activity, which can be extracted from the seeds of the plant *Caesalpinia gilliesii* (Wall), a glandular shrub found in the Southwestern United States, particularly in Arizona.

The seeds of many plants have been the source of proteins and glycoproteins which affect the growth and division of cells. They have been used as a probe for the components of cell surfaces, for the stimulation of cell division, and in studies of cytotoxic effects.

Cesalin is an oligomeric protein of undetermined structure, having a molecular weight of about 110,000. Hence it may be regarded broadly as a biopolymer. Several types of biopolymers that exhibit antitumor activity have been derived from plant materials. They may be polysaccharides, such as lentinan, a glycan isolated from *Lentinus edodes*, scleroglucan isolated from *Sclerotium glucanicum*, or proteins, such as cesalin.

A process for the extraction and purification of cesalin derived from the plant *Caesalpinia gilliesii* (Wall) is described in an article by A. Ulubelen, et al., J. Pharm. Sciences, Vol. 56, No. 7, pages 914–916 (July 1967). The cesalin obtained by these authors displayed activity against Walker carcinosarcoma 256 in rats and sarcoma 180 in mice. It was obtained by extracting the dry pods (whole seeds) with water at room temperature, lyophilizing the aqueous extract to obtain a crude powder which was redissolved in water, defatted with ether, and precipitated with ethanol, dialyzed against water, and the resulting dialysate lyophilized to yield a product having antitumor activity. Fractions were separated by column chromatography using ion exchange resins and synthetic dextran derivatives (Sephadex G-200) as chromatographic supports. Six fractions were subjected to paper electrophoresis, and their saccharide content detected by paper chromatography. Various protein peaks were observed, indicating that the original extract comprised a mixture of several proteins and/or glycoproteins differing in their content and distribution of amino acids, thus representing a partially purified cesalin, which was only moderately active against Walker 256 carcinosarcoma and sarcoma 180.

GENERAL DESCRIPTION OF THE INVENTION

In accordance with the present invention there is provided a novel and improved process for the extraction of cesalin from either the whole seeds or from the endosperm of *Caesalpinia gillespii*, and the purification of the crude cesalin to yield a specific protein product of electrophoretic purity, which is highly active against Walker 256 intramuscular tumors in rats at dosages as low as 3 $\mu$g/kg of body weight. This high purity cesalin exhibits greater effectiveness, in contrast to the less active mixtures of proteins and other materials obtainable by prior art methods.

While the starting material may be either the whole seed, or the endosperm which has first been separated from the seed, the endosperm is preferred, for reasons described more fully below.

The novel method of extraction employed in accordance with the invention comprises these steps:

(1) the whole seeds (ovules) of *Caesalpinia gilliesii* are subjected to mechanical disruption to separate the endosperm from the seed coat, for example by comminution in a hammer mill;

(2) the endosperm is extracted with a lipid solvent such as the halogenated aliphatic hydrocarbons, to remove therefrom an irritant oily lipid, leaving a meal or powder of defatted crude endosperm;

(3) the crude endosperm is extracted with water to recover therefrom water-soluble protein components;

(4) depending upon the purity of the extract from step (3), optionally, the water extract of the endospearm is dialyzed against water and the non-dialyzable portion is centrifuged to give a precipitate and a supernatant portion;

(5) the supernatant portion is acidified to a pH of about 4.5–5.0 or saturated with ammonium sulfate to form a precipitate of crude cesalin, and a second supernatant. Any acid may conveniently be used for this purpose.

In accordance with the purification aspect of the invention, the crude cesalin is purified by treatment by gel filtration and recovery therefrom by elution. It may be still further purified by removal of associated carbohydrates by rechromatography, for example, on hydroxyl apatite. The remaining carbohydrate, if any, is a hexosan (about 0.1 to 0.3%).

The other protein fractions may be similarly purified. Some are of slightly lower molecular weight than pure cesalin, and some of larger molecular weight, but dissociable into sub-units of about the same size as those from cesalin. These associated proteins showed no antitumor activity against Walker 256 carcinosarcoma in rats.

The yield of pure cesalin is of the order of 0.1% of the weight of the defatted seed meal.

The pure cesalin, molecular weight 110,000, migrates as a single component by gel electrophoresis in a non-disociating polyacrylamide gel at pH 4.3. It is active against Walker 256 tumor in vivo in rats with T/C of about 180–260 at 12–3 $\mu$g per kg per day, but is toxic at higher concentrations.

The lipid solvent may be, for example, ethylene dichloride or trichloroethane.

In accordance with another aspect of the invention, the extraction and purification steps may be applied to the whole seeds of the plant, but this may present a problem in the concomitant solubilization of plant gum from the seed coat, which is not easily separated from the endosperm by mechanical means. There is also a significantly higher carbohydrate content in the crude cesalin from whole seeds than in that from the endosperm. However, in either case, the crude cesalin is obtained in the first instance by precipitation from the non-dialyzable solution either by acidification to pH 4.8 with acetic acid or by saturation with ammonium sulfate, the acidification procedure being preferred.

DESCRIPTION OF THE PREFERRED EMBODIMENT

Figure 1A:
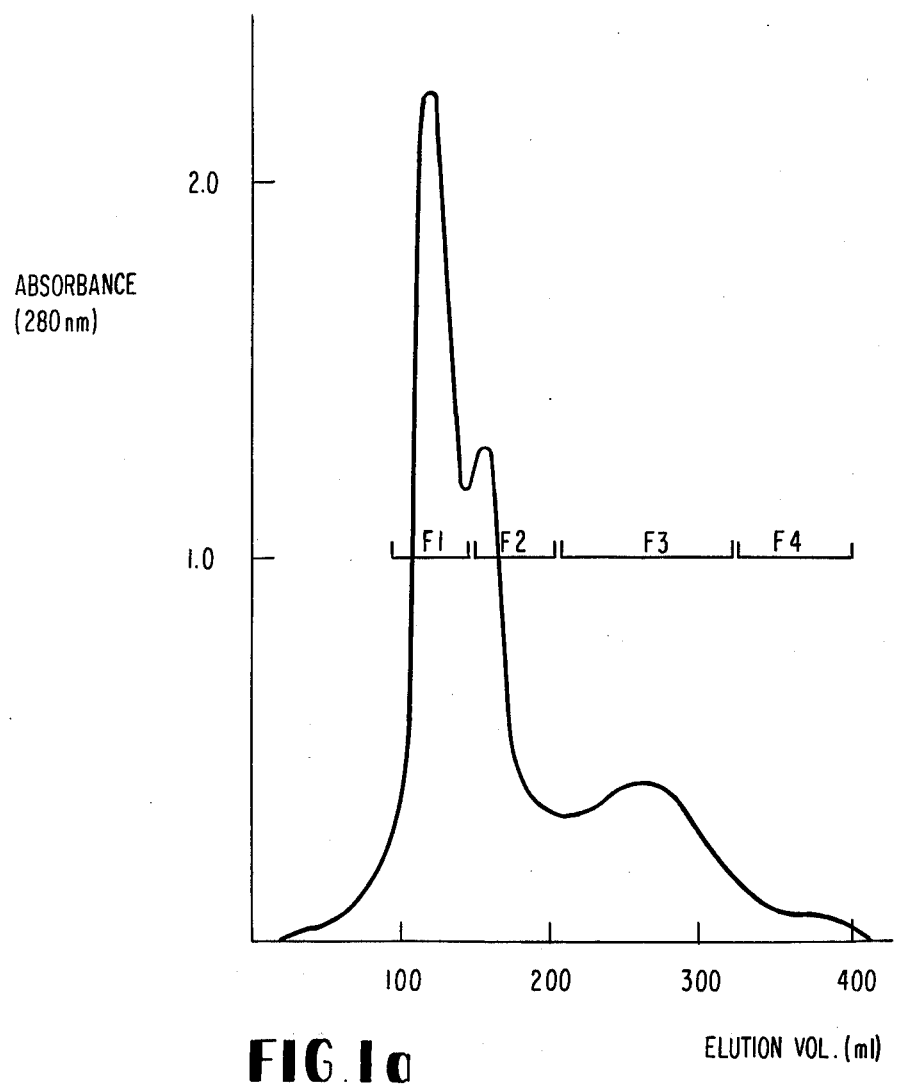

The following examples illustrate the presently preferred practice of the invention, but are not to be regarded as limiting the invention thereto.

In the examples, the operations are performed at room temperature unless otherwise indicated.

Gel electrophoresis is carried out by the procedure of Reisfield et al. Nature 195; 281 (1962). The resulting gel is stained by Coomassie Blue for protein and periodic acid-Schiff (PAS) for carbohydrate, according to the method of Zacharius et al. Anal. Biochem. 3: 148 (1969).

Carbohydrate is determined by the phenol-sulfuric acid method (Anal. Chem. 28: 350-356 (1956).

The molecular weight of proteins is estimated by column chromatography on Sephadex G-100 for intact protein (Biochem. J., 96 595 (1965)), and by SDS-gel electrophoresis for dissociated proteins (J. Biol. Chem. 244: 4406 (1969)).

Antitumor tests were performed with Walker 256 intramuscular tumors in rats according to methods based on the National Cancer Institute screening protocol.

EXAMPLE 1

Fractionation of Water Extract from Endosperm of C. gilliesii

The endosperm (23.0 g) obtained by hand dissection of C. gilliesii seeds (50.0 g) was ground in a Waring blender for about 90 secs and the meal was extracted twice at room temperature with ethylene chloride (150 ml), for 30 min. each time. The resulting powder (15.3 g) was sequentially extracted at 5° C., once with 150 ml. of water for 30 minutes, and once with 150 ml of 0.05 M phosphate buffer (pH 7.4) for 30 minutes. The combined extracts were dialyzed against distilled water for 3 days at 5° C. and the non-dialyzable fraction was centrifuged to give a precipitate (E-1, 2.27 g). The supernatant was acidified with acetic acid at room temperature to pH 4.8 to give a precipitate (E-11, 1.17 g). The supernatant was freeze dried (E-III, 0.70 g). Instead of acid precipitation, ammonium sulfate was also used for fractionation; the non-dialyzable fraction described above was saturated with ammonium sulfate to give a precipitate (E-IV, 1.13 g from 50 g of seeds).

EXAMPLE 2

Fraction of Water Extract from Defatted Whole Seed Meals

The defatted meals from whole seeds (50.0 g) was extracted with 1 liter of water for 30 minutes at 5° C. The aqueous extract was dialyzed for 3 days at 5° C. The non-dialyzable fraction (M-11 containing 2.0-2.5 g of solute) was acidified with acetic acid to pH 4.8 forming a precipitate (M-II, 1.21 g). The supernatant was freeze dried (M-III, 0.83 g).

The principal fractions were analyzed for carbohydrate content. Gel electrophoresis of these fractions indicated the presence of five protein bands, identified A, B, C, D and G, with only band B showing a positive reaction for carbohydrate by PAS. An estimate was made of the protein composition of the original aqueous extract of the endosperm by densitometric scanning of 600 nm of the Davis gels, stained by Coomassie blue, which indicated 7.0% A, 46.6% B, 14.5% C, 10.3% D, 11.6% G, and other minor bands totalled 4.9%. Component D was identified with cesalin. Components B and C had no antitumor activity against Walker 256.

EXAMPLE 3

Purification of Cesalin from Fraction E-11

Figure 1B:
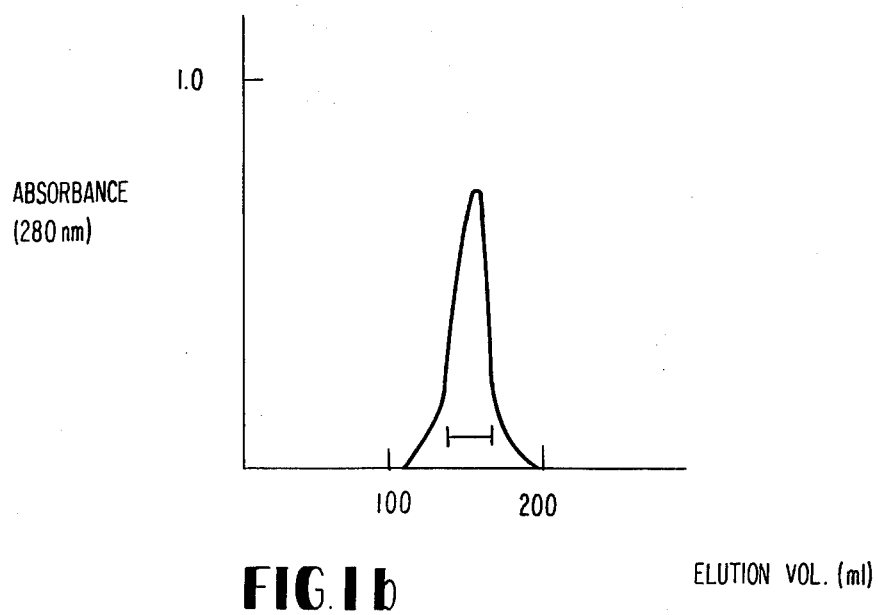

A sample E-II (200 mg) was fractionated on a column of Sephadex G-100 as shown in FIG. 1a. The yields for each fraction were F-1, 64 mg; F-2, 42 mg; F-3, 47 mg; F-4, 11 mg. Gel chromatography showed F-1 with components B and D, F-2, mainly component D, F-3, mainly component G, and F-4 contained no protein. Rechromatography of fraction F-2 as shown in FIG. 1b gave cesalin (31 mg).

Figure 2:
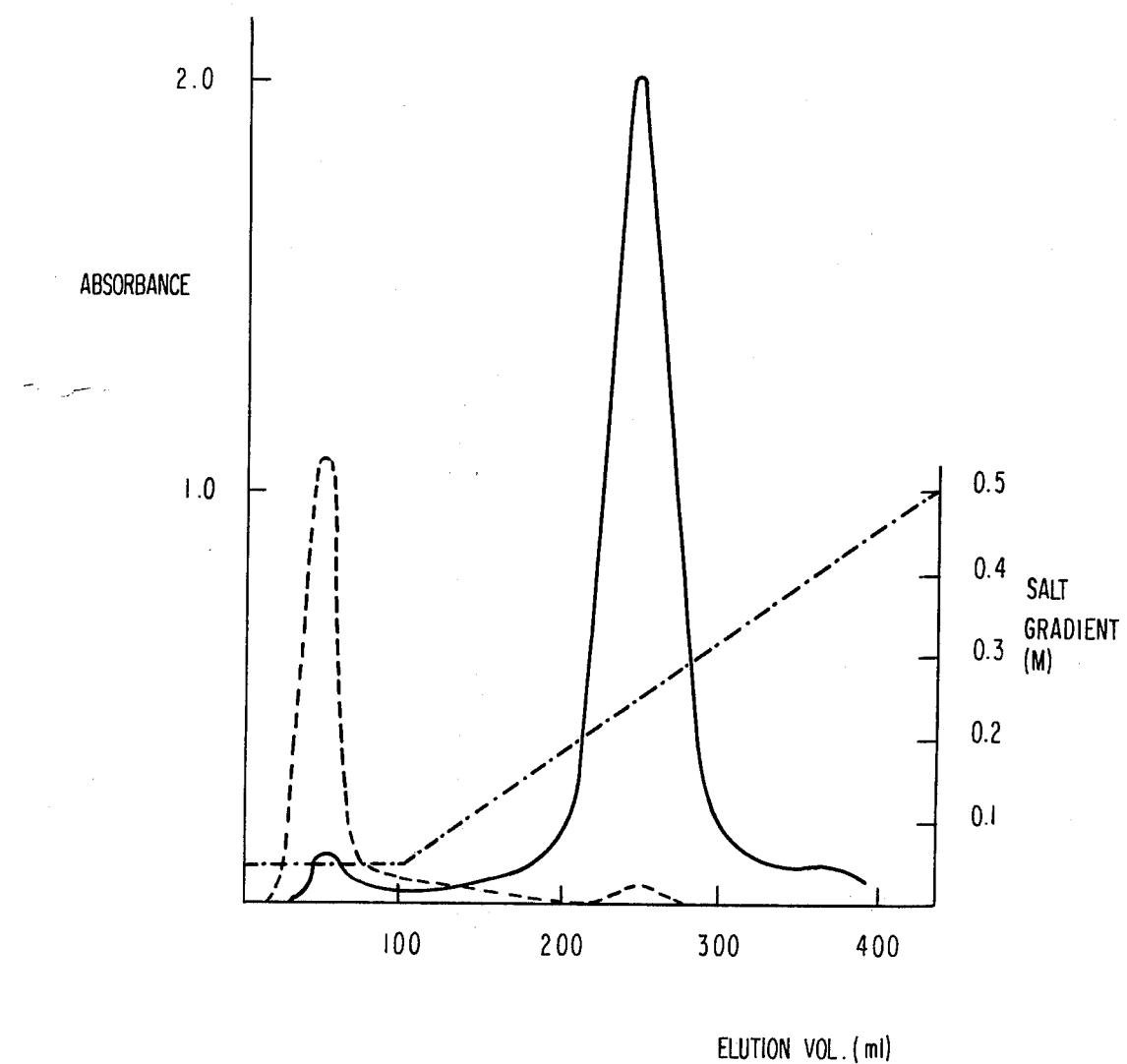

The cesalin from rechromatography contained 1.4% of carbohydrate. Chromatography on hydroxylapatite was carried out for further purification (FIG. 2) where it is seen that most of the carbohydrate was not absorbed. However, the purified protein still contained 0.3% carbohydrate. This protein was cesalin, showing maximum ultraviolet adsorption at 278 nm, and $E_{280}^{1\%}$ nm 10.09. It had molecular weight of approximately 110,000 by column chromatography and sub-units, which corresponded to molecular weights of approximately 28,000 to 30,000.

EXAMPLE 4

Extraction of Cesalin from Whole Seeds

The seeds of Caesalpinia gilliesii were ground on a hammer mill. A portion (3 kg) of ground seeds of C. gilliesii was stirred in trichloroethylene (19 liter) for 30 minutes at room temperature and then allowed to settle for approximately 30 minutes. The endosperm floated on the surface and was skimmed off into another tank containing trichloroethylene (19 liter) where the mixture was stirred for 15-20 minutes before allowing to settle. The endosperm was skimmed off and filtered under vacuum before transferring a half to a Waring blender where it was blended in trichloroethylene (1600 ml) for 25 seconds on low speed. The suspension was transferred to a 2 liter measuring cylinder in which the small amount of remaining seed coat sank to the bottom. The suspension of endosperm was filtered and the filtrate used to blend the second half of endosperm as before. The filtered endosperm was washed in the Buchner funnel with trichloroethylene (400 ml). The washed endosperm was air-dried in a fume-hood.

The trichloroethylene used for the initial suspending of the ground seed was used for a total of 15 kg of material before discarding. The trichloroethylene used for the second suspension was then used for the initial suspension and fresh trichloroethylene used for the second suspension. In this manner 20 gallons of solvent served to separate 21.86 kg of ground seeds to yield 6.92 kg dry crude endosperm, which was nearly free from seed coat particles.

Defatted crude endosperm (500 g) was suspended by stirring with 5000 ml of water at 4° C. for 30 min. The suspension was filtered through cheese cloth to remove large particles and then passed through a Sharples centrifuge. The clear supernatant was brought to pH 4.8 with glacial acetic acid. After 1.5 hr. at 4°, the precipitate was collected by aspiration of the clear supernatant and centrifugation of the remaining suspension at $8000 \times g$ at 4° for 20 min. The precipitate was suspended with stirring for 15-30 min. in 30 ml of water, to which was added 30 ml of water, to which was added 30 ml of 0.1 M phosphate buffer pH 7.6, containing 0.8 sodium chloride and 0.02 M mercaptoethanol. The mixture was centrifuged and the supernatant adjusted to pH 4.9 before being centrifuged again at $27,000 \times g$ for 30 min. The light yellow supernatant was subjected to gel filtration immediately on a column ($90 \times 7.7$ cm) of Sephadex G-100 that was equilibrated and subsequently eluted with the same solvent (0.05 M phosphate buffer, pH 7.6 containing 0.4 M sodium chloride and 0.01 M mercaptoethanol). Two major peaks were obtained, the second peak, containing cesalin, eluted in fractions corresponding to an elution volume of 1600 to 2000 ml. The cesalin-containing fractions were identified by gel electrophoresis at pH 4.3. The fractions in the cesalin peak were combined, dialyzed against water and freeze dried. The residue was rechromatographed on Sephadex G-100 as before to give pure cesalin. The yield was 0.05–0.1% w/w of the defatted crude endosperm.

The in vivo test results on the pure cesalin from the foregoing examples are summariced below:

| Walker 256 in rats | |
|---|---|
| Cesalin | T/C |
| µg/kg | |
| 25 | 142 |
| 12.5 | 183 |
| 6.3 | 257 |
| 3.1 | 264 |

The seeds of the plant *Caesalpinia gilliespii* are generally flat, about the size of a finger nail and about ⅛ inch in thickness. They are extremely hard and must be broken up by a device having good shearing action. While a hammer mill was used, other suitable equipment may also be employed as will be apparent to those skilled in the art.

The extraction step with the lipid solvent may be conveniently carried out at room temperature. A halogenated aliphatic hydrocarbon may be preferred especially in those operations as shown in example 4 where a floation technique is employed.

With regard to the water extraction step, any suitable temperature above zero may be used, such as 5° C. to 15° C.

Further modifications or variations will be apparent to those skilled in the art from the foregoing detailed description of the invention.

What is claimed is:

1. A process for obtaining a proteinaceous extract of about 110,000 molecular weight having antitumor activity from the *Caesalpinia gillesii* plant comprising the steps of:
    (1) subjecting the whole seed of *Caesalpinia gillesii* to mechanical disruption to separate the endosperm and the seed coat portions and removing the seed coat portion;
    (2) extracting the endosperm portion with a halogenated aliphatic hydrocarbon solvent to remove therefrom an oily lipid, leaving defatted crude endosperm;
    (3) extracting the crude defatted endosperm with water to recover those protein components extractable with water;
    (4) dialyzing the water extract against water, and separating the non-dialyzable portion into a precipitate and a supernatant portion;
    (5) treating said supernatent portion with an acid to acidify said portion to a pH of about 4.5–5.0 or saturating it with ammonium sulphate to form a precipitate of crude proteinaceous extract and recovering the crude proteinaceous extract;
    (6) purifying the crude proteinaceous extract by gel filtration and recovering therefrom by elution.

* * * * *